US008809288B2

(12) United States Patent
Baier et al.

(10) Patent No.: US 8,809,288 B2
(45) Date of Patent: Aug. 19, 2014

(54) METHOD FOR INCREASING IMMUNOREACTIVITY

(75) Inventors: Gottfried Baier, Innsbruck (AT); Hans Loibner, Vienna (AT); Manfred Schuster, Schrick (AT); Gunther Lametschwandtner, Vienna (AT); Dominik Wolf, Mutters/Raitis (AT)

(73) Assignees: Medizinische Universitat Innsbruck, Innsbruck (AT); Apeiron Biologics AG, Vienna (AT)

( * ) Notice: Subject to any disclaimer, the term of this patent is extended or adjusted under 35 U.S.C. 154(b) by 0 days.

(21) Appl. No.: 12/747,326

(22) PCT Filed: Dec. 10, 2008

(86) PCT No.: PCT/AT2008/000443
§ 371 (c)(1),
(2), (4) Date: Jun. 10, 2010

(87) PCT Pub. No.: WO2009/073905
PCT Pub. Date: Jun. 18, 2009

(65) Prior Publication Data
US 2010/0260808 A1 Oct. 14, 2010

(30) Foreign Application Priority Data
Dec. 10, 2007 (AT) ................ A 1996/2007

(51) Int. Cl.
*A61K 48/00* (2006.01)
*C07H 21/02* (2006.01)
*C07H 21/04* (2006.01)

(52) U.S. Cl.
USPC ........................... 514/44; 536/23.1; 536/24.5

(58) Field of Classification Search
None
See application file for complete search history.

(56) References Cited

U.S. PATENT DOCUMENTS

| 2005/0037989 A1* | 2/2005 | Lewis et al. ............... 514/44 |
| 2006/0292119 A1 | 12/2006 | Chen et al. ............... 424/93.2 |
| 2007/0054055 A1 | 3/2007 | Hsiao et al. ............... 427/372.2 |
| 2007/0054355 A1 | 3/2007 | Reiss et al. ............... 435/69.1 |
| 2007/0087988 A1 | 4/2007 | Sawasdikosol et al. .... 514/44 A |
| 2007/0274915 A1* | 11/2007 | Rao et al. ............... 424/9.2 |

FOREIGN PATENT DOCUMENTS

| WO | WO 2004/078130 | 9/2004 |
| WO | WO 2008/033403 | 3/2008 |

OTHER PUBLICATIONS

Naramura et al., "c-Cbl and Cbl-b regulate T cell responsiveness by promoting ligand-induced TCR down modulation," *Nature Immunology*, 3(12): 1192-1199, 2002.
Office Communication issued in Chinese Patent Application No. 20080120180, dated Nov. 24, 2011.
Chiang et al., "Ablation of Cbl-b provides protection against transplanted and spontaneous tumors," *J. Clin. Invest.*, 117(4): 1029-1036, 2007.
Loeser and Penninger, "The Ubiquitin E3 Ligase Cbl-b in T Cells Tolerance and Tumor Immunity," *Cell Cycle*, 6(20): 2478-2485, 2007.
Office Communication issued in Singapore Patent Application No. 20100400-4, mailed on Sep. 16, 2011.
Chiang et al., "Ablation of Cbl-b provides protection against transplanted and spontaneous tumors," *J. Clin. Invest.*, 117:1029-36, 2007.
Lametschwandtner et al., "Development of an effective cancer immune therapy by Cbl-b silencing," *J. Immuno.*, 31:943, 2008.
Loeser et al., "Spontaneous tumor rejection by cbl-b-deficient $CD8^+$ T cells," *JEM*, 2007.
Yuan, Jianda et al., "CTLA-4 blockade enhances polyfunctional NY-ESO-1 specific T cell responses in metastatic melanoma patients with clinical benefit," *Proceedings of the National Academy of Sciences*, 105(51):20411-20415, 2008.
Ahmadzadeh, Mojgan et al., "Tumor antigen-specific CD8 T cells infiltrating the tumor express high levels of PD-I and are functionally impaired," *Blood*, 2009(114):1537-1544, 2009.
Ma, Daphne Y., and Clark, Edward A., "The role of CD40 and CD40L in Dendtritic Cells," *Seminars in Immunology*, 21(5): 265-272, Oct. 2009.
Gladue, Ronald P. et al., "The CD40 agonist antibody CP-870,893 enhances dendritic cell and B-cell activity and promotes anti-tumor efficacy in SCID-hu mice," *Cancer Immunology, Immunotherapy*, 60:1009-1017, 2011.
De Paola et al., "Restored T-cell activation mechanisms in human tumour-infiltrating lymphocytes from melanomas and colorectal carcinomas after exposure to interleukin-2," *British Journal of Cancer*, 88(2):320-326, 2003.
Mittendorf, "Evaluation of the CD107 cytotoxicity assay for the detection of cytolytic CD8+ cells recognizing HER2/neu vaccine peptides," *Breast Cancer Research and Treatment*, 92(1):85-93, 2005.
Parmiani et al., "Cytokines in cancer therapy," *Immunology Letters*, 74(1):41-44, 2000.
Rosenberg, "The emergence of modern cancer immunotherapy," *Annals of Surgical Oncology*, 12(5):1-3, 2005.
Schroder et al., "Interferon-gamma: an overview of signals, mechanisms and functions," *Journal of Leukocyte Biology*, 75(2):163-189, 2004.
Segura et al., "ICAM-1 on exosomes from mature dendritic cells is critical for efficient naive T-cell priming," *Blood*, 106(1):216-223, 2005.

(Continued)

*Primary Examiner* — Amy Bowman
(74) *Attorney, Agent, or Firm* — Fulbright & Jaworski LLP

(57) ABSTRACT

The invention relates to an in vitro or ex vivo method for increasing the immunoreactivity of cells of the immune system, which were contacted with an antigen, said method comprising the reduction or inhibition of the Cbl-b function of said cells, thereby increasing the immunoreactivity of the cells towards the antigen.

20 Claims, 10 Drawing Sheets

(56) References Cited

OTHER PUBLICATIONS

Van Kooten and Banchereau, "CD40-CD40 ligand," *Journal of Leukocyte Biology*, 67:2-17, 2000.

Office Action issued in Chinese Application No. 200880120180.X, dated Jan. 14, 2013.

Chiang et al., "Ablation of Cbl-b provides protection against transplanted and spontaneous tumors", *The Journal of Clinical Investigations*, 112(4):1029-1036, 2007.

Office Action issued in Japanese Patent Application No. 2010-537207, issued Jun. 18, 2013.

Vonderheide and June, "A Translational Bridge to Cancer Immunotherapy", *Immunologic Research*, 27(2-3):341-355, 2003.

Office Action issued in Japanese Application No. 2010-537207, dated Feb. 4, 2013.

Morris et al., "Enhancing siRNA effects in T cells for adoptive immunotherapy", *Hematology*, 10(6):461-467, 2005.

\* cited by examiner

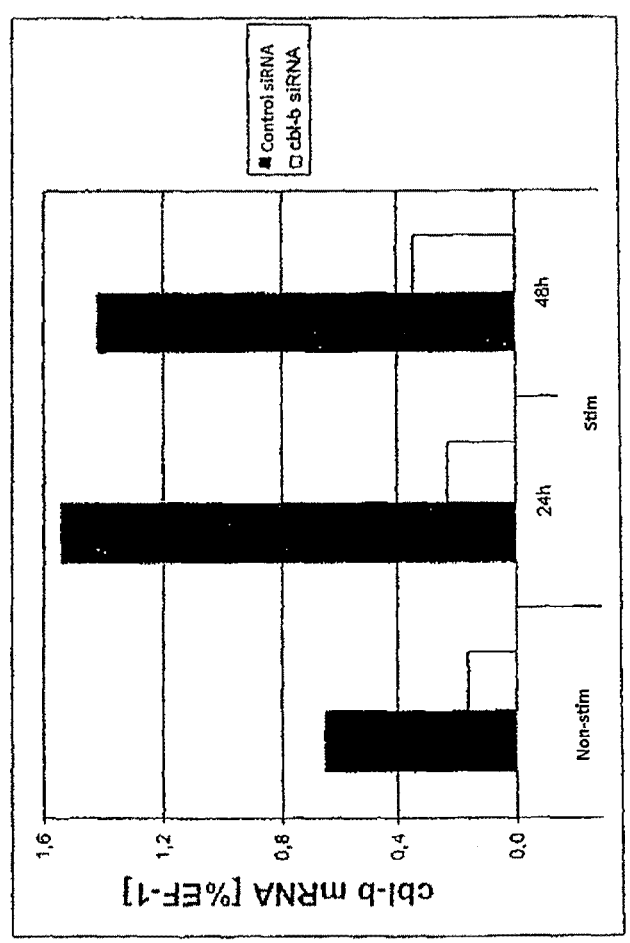

METHOD FOR INCREASING IMMUNOREACTIVITY

This application is a national phase application under 35 U.S.C. §371 of International Application No. PCT/AT2008/000443 filed 10 Dec. 2008, which claims priority to Austrian Application No. 1996/2007 filed 10 Dec. 2007. The entire text of each of the above-referenced disclosures is specifically incorporated herein by reference without disclaimer.

The present invention relates to methods for modulating the immune response of cells.

Active immunization made possible for the first time a comprehensive fight against the most threatening infectious diseases and even achieved world-wide eradication in some cases using an inexpensive and highly efficient endogenous defense mechanism. Therefore, efforts have been and will be undertaken to develop prophylactic and therapeutic vaccination approaches against various indications. However, efficient immunization requires induction of an immune response, which leads to a protective immunity. However, lack of immunogenicity of the immunization antigen leads to failure of the desired effect to occur. Highly interesting and specific antigen formulations have already been developed for prevention and treatment of malaria, HIV, influenza or tumor diseases, to name but a few prominent examples. However, these treatments have not been successful, for example, due to lack of immunogenicity of the immunization antigen. Furthermore, even widely used vaccines lead to problems of lack of immunogenicity, such as the hepatitis B vaccines, which actually build up a protective immune response titer only for approximately 80% of those treated. The main reason for the lack of reactivity of the immune system is that these antigens are not recognized as being "foreign". In mammals, it is mainly Tcells which decide whether a structure presented by antigen-presenting cells (APCs) will be recognized as endogenous or foreign. To induce an immune response, essentially two separate signals, independently of one another, are necessary. This mechanism should prevent overshooting of the immune system. The first prerequisite is for the T-cell receptor to also recognize the antigen offered by the APC. If this is not the case, then no further reaction will take place. Furthermore, for induction of an immune response, it is absolutely essential to have an interaction of the CD28 receptor on the T-cell surface with B7 expressed on the APC only when the latter classifies the antigenic structure as dangerous. In the case of vaccination with a vaccination antigen having only marginal immunogenicity, co-stimulation via the interaction between B7 and CD28 mail fail to occur, which does not subsequently lead to an immune response, but instead leads to the development of a tolerance on a T-cell level. However, it has been demonstrated that the need for co-stimulation can be bypassed by turning off the enzyme E3-ubiquitin ligase Cbl-b. This enzyme is a decisive switch point in control of the immunoreactivity (Chiang et al., J Clin Invest (2007) doi:10.1172/JCI29472). However, in the absence of Cbl-b, administered substances that are hardly immunogenic may lead to induction of a strong immune response. Furthermore, Cbl-b-deficient mice (homozygotic gene knockouts) are viable and their immune system is capable of efficiently recognizing autologously induced tumors and building up a lytic immune response based mainly on CD8+ T-cells (Loeser et al., JEM (2007) doi:10.1084/iem.20061699). However, the complete elimination of the enzyme, which has been described, also leads to an increased autoimmunity after immunization with superantigens. Loeser et al. have thus been able to show that Cbl-b as a negative regulator is responsible for the "immunoreactivity" of T-cells.

SiRNA technology for attenuation of specific gene expression has also been described already for Cbl-b with a lower efficiency. US 2007/0087988 relates to a method for regulating HPK1, the expression of which can be increased by increasing Cbl-b expression and vice versa (e.g., by inhibition of Cbl-b siRNA).

US 2007/00543355 describes Cbl-b peptides and Cbl-b-associated proteins, in particular POSH, and their use for treatment of Cbl-b-associated diseases.

WO 2004/078130 A2 relates to compositions for treatment of POSH-associated diseases, such as viral diseases, cancer and neurological disorders. POSH can be made available together with a plurality of POSH-associated proteins, including Cbl-b.

US 2006/0292119 A1 relates to methods for increasing the immune response of immune cells by inhibition of negative immunoregulators in the cell. Such negative immunoregulators are selected from proteins, which are associated with molecular stability, e.g., by ubiquitination, deubiquitination and sumoylation as well as transcription factors, which inhibits the expression of NFkB inhibitors, or suppressors of transcription of NFkB target genes.

However, no use of Cbl-b mediators for clinical applications has been described. Therefore, one goal of the present invention is to make available a method for modulating the immunoreactivity that is suitable for practical use.

The present invention therefore relates to an in vitro or ex vivo method for increasing the immunoreactivity of cells of the immune system, which were contacted with an antigen, comprising a reduction in or inhibition of the Cbl-b function of these cells, thereby increasing the immunoreactivity of the cells to the antigen.

The Cbl-b gene and its gene products have been described in detail in the related art (UniGene Id. Hs.3144 and Hs.381921). Cbl-b sequences have been published in the GenBank database, for example, under Acc. No. NM_008279 and NP_009112. Anti-Cbl-b antibodies, siRNAs and antisense inhibitors are available commercially. Certain siRNAs are suitable for reducing or inhibiting Cbl-b expression and thus also Cbl-b function are disclosed in US 21007/0054355 with mixed RNA/DNA nucleotides and a length of approximately 20 bases, for example.

To counteract the risk of an overreaction of the immune system, which can lead to induction of autoimmune reactivity, for example, the inhibition/knockout of Cbl-b functions in T-cells can take place only in a strictly defined period of time. Therefore, it is essential for an adjuvant therapeutic vaccination approach to attenuate Cbl-b in a controlled manner only for a limited period of time to support the development of an immune response specific for a given immunization antigen but to prevent an autoimmune disease by promptly restoring the "normal" immunological state. Therefore, according to the present invention, only a certain selection of isolated cells of the immune system is treated in vitro or ex vivo and then returned to the patient. One approach for efficient in vitro or ex vivo Cbl-b attenuation is therefore the prerequisite for increasing the immunoreactivity.

The Cbl-b function is preferably reduced or inhibited by reducing or inhibiting the expression of Cbl-b. The terms reduction or inhibition related to the reduction in the function (and/or expression) of Cbl-b in comparison with the unchanged natural function up to complete inhibition of function. The function (and/or expression) is preferably reduced by at least 30%, 40%, 50%, 60%, 70%, 80%, 90% or 95%.

In preferred embodiments, the function of Cbl-b is preferably reduced or inhibited transiently. In other words, the function is reduced only temporarily as indicated above and subsequently can recover, for example, by consumption or degradation of inhibitors, such as Cbl-b siRNA or by neogenesis or non-Cbl-b-impaired cells (in vivo). The transient reduction in Cbl-b in immune cells can also be achieved repetitively, e.g., until a therapeutic success is achieved.

The expression of Cbl-b is preferably reduced or inhibited by using Cbl-b antisense RNA or siRNA. To this end, short DNA and/or RNA sequences that were complementary to a portion of the target (Cbl-b) mRNA sequence are used, so that they thus hybridize with them and inactivate them. The length of these sequences is preferably at least 15, 18, 20, 22, 25, 28, 30, 35, 40, 50, 60, 70, 80, 90, 100, 120, 140, 160, 180 or 200 bases up to the complete target sequence, preferably up to 2502, 2000, 1500, 1000, 500 or 300 bases. The sequences of SEQ ID nos. 1, 2, 3, 4, 5, 6, 7 and/or 8 are preferably used.

Likewise the function of Cbl-b can be reduced or inhibited by a plurality of other known components, such as by using Cbl-b antagonists, inhibitors, in particular aptamers or intramers. Andy antagonists or inhibitors which suppress the effect and/or the function of Cbl-b may also be used according to the invention to increase the immunoreactivity of the cells. Antagonists or inhibitors are preferably used to produce a pharmaceutical agent for the inventive in vitro, ex vivo or even in vivo increase in the immunoreactivity of cells of the immune system. This permits treatment of diseases with a suppressed or inefficient immune system, in particular cancer, as well as the increase in the immune response to (vaccination) antigens which can be contacted with the cells of the immune system in vivo or ex vivo The present invention also relates to a method for reducing the immunoreactivity of cells of the immune system, comprising the reduction or inhibition of the c-Cbl function of the cells, so that the immunoreactivity of the cells to the antigen is reduced, preferably by transient reduction or inhibition, in particular by using c-Cbl antisense RNA or siRNA. To increase the immunoreactivity, it is not absolutely necessary to attenuate c-Cbl jointly together with Cbl-b. As shown in the examples, attenuation of c-Cbl instead yields a reversal in the effects achieved by inhibition of Cbl-b. Cbl-b and c-Cbl therefore have antagonistic functions. C-Cbl also fulfills a previously unknown function in the fine regulation of the T-cell reactivity in that its attenuation leads to an increased immune tolerance. Therefore the reduction in or inhibition of the c-Cbl function is suitable for immunosuppression and therefore allows its use in inflammations or allergies, for example. Since the extent and direction of the attenuation depend on the dose in reduction of or inhibition of Cbl-b and/or c-Cbl (analogous to Cbl-b as described herein), both factors may be reduced in their function in combination. To increase the immunoreactivity, the reduction in Cbl-b outweighs the reduction in c-Cbl and vice versa. C-Cbl antisense or siRNA may have the same sequence lines as those described above for Cbl-b. The sequences of SEQ ID Nos. 9, 10, 11, 12, 13, 14, 15 and/or 16 are preferably used.

In special embodiments, cells which have taken up the antigen and preferably present an antigen fragment or, even better, recognize an antigen fragment in the context of HLA and are thereby activated are used in particular.

In preferred embodiments, the cells to be used according to the invention are antigen-presenting cells, PBMCs (peripheral blood mononuclear cells), T-lymphocytes, B-lymphocytes, monocytes, macrophages and/or dendritic cells, in particular T-lymphocytes, CD8+ T-lymphocytes, CD4+ T-lymphocytes, in particular Th1, Th2, Th17, Tregs (regulatory T-cells) or CTL (cytotoxic T-cells), NK cells or NKT cells. Likewise, it is also possible to use CD3/CD19-negative lymphocytes in general. NK cells form an especially preferred group thereof. The antigen has preferably been taken up by the cells and they present it, preferably an antigen fragment. PBMCs and T-cells are especially preferred in combination for treatment to induce an especially strong antigen-specific reaction. In other embodiments, in particular for a general increase in immunoreactivity (e.g., for treating an immune insufficiency), various T-cells alone are sufficient to achieve a broad effect. The increased immunoreactivity according to the invention is preferably mediated by these cells, in particular CD8 or CD4 cells as well as NK and/or NKT cells.

Electroporation is preferably used for transfection of cells, in particular T-cells, or NK cells with a Cbl-b inhibitor such as Cbl-b siRNA or a knockout Cbl-b construct. Any media which lead to transfection, i.e., to inhibition of Cbl-b, may be suitable for this purpose. Optimem (Gibco, #31985-047) is an example of one such medium.

In addition, the cells may also be treated, i.e., stimulated with an immunostimulating substance, e.g., an immunostimulating cytokine or ligand of other immunostimulating receptors (such as TLRs, toll like receptors) or antibodies to surface molecules, preferably CD3 and/or CD28, to promote an immune response by the cells.

Inhibition of Cbl-b may also be used as part of a vaccination supported by dendritic cells, preferably an anti-tumor vaccination.

As an alternative and/or in addition, the cells that inhibit in vitro co-culturing of Cbl-b-inhibited cells with dendritic cells that have been obtained from the patient and have preferably been loaded with tumor (cell) antigens, as it is also possible to use the co-culture for the inventive purposes.

"Vaccination" as used herein is not to be understood in the absolute sense—i.e., administration of an immunogen which leads to absolute protection by the immune system—but rather as immunological administration to increase protection by the immune system and/or to activate the immune system, in particular the cells thereof against the vaccine antigen.

In one particular aspect, the present invention relates to the use of Cbl-b inhibitors or antagonists for production of a pharmaceutical composition to increase the immunoreactivity to an antigen in a patient and/or increasing the immunoreactivity per se, comprising the isolation of cells of the immune system of a patient, an in vitro or ex vivo increase in the immunoreactivity by using Cbl-b inhibitors or antagonists and reimplanting the cells in the patient, wherein the immunoreactivity is increased by a reduction in or inhibition of the Cbl-b function of the cells.

Implementation of the increase in immunoreactivity, preferably for a limited period of time, concurrently with a vaccination, administration of the antigen, can be induced by reducing Cbl-b expression in a small portion of the circulating T-cells. PBMCs (peripheral mononuclear blood cells) may be obtained from whole blood and/or blood cells from the bone marrow and from the tumor tissue itself (TILS) of the patient, ideally having been immunized a few days previously, e.g., five days, and treated in vitro or ex vivo with a Cbl-b-specific siRNA attenuation batch. This method is performed very rapidly. In the ideal case, this cell preparation may be administered to the patient again only a few minutes after having been removed. The cells may optionally be multiplied or expanded by ex-vivo-stimulation protocols suitable for the respective cells before the cells are reimplanted. The T-cells activated in vitro, representing only a few percent of the patient's T-cell population, encounter antigen-presenting cells in lymph nodes while circulating in the recipient organism, where these antigen-presenting cells have taken up antigens due to the immunization that has already occurred and have migrated there. Since the T-cells treated in vitro do not require a co-stimulation signal, they proliferate immediately after recognition of the immunization antigen and secrete cytokines, which contribute systemically to induction of an immune response on both a cellular level and a humoral level. With this batch, even weakly immunogenic antigens will lead to the establishment of a long-lasting immune protection. Likewise, rejection of autologous tumors in cancer patients can be induced in this way. A Cbl-b antagonist here increases the immunoreactivity, where this is used either in an exclusive and/or a concomitant chemotherapy/radiotherapy in combination with passive immunizations, such as tumor-antigen-specific antibodies.

This method is therefore used for treating congenital or acquired immune insufficiency, in particular AIDS, multiple myeloma, chronic lymphatic leukemia, drug-induced immunosuppression or a cancer, optionally with the selection of disease-specific antigens. Treatment of a cancer involving solid tumors is preferred in particular.

To increase the chance of success of a treatment, the treatment of a cancer is preferably administered in combination with another anti-tumor therapy, in particular chemotherapy, radiotherapy, administration of a therapeutic biological or dendritic cell-supported (tumor) vaccination. Inhibition of Cbl-b can be used as part of a dendritic cell-supported vaccination, preferably an anti-tumor vaccination. As an alternative and/or in addition, in vitro co-culturing of Cbl-b-inhibited cells with dendritic cells obtained from the patient, preferably having been loaded with tumor (cell) antigens, is also possible, as well as the use of the co-culture for the inventive purposes.

The in vitro or ex vivo increase in the immunoreactivity may be performed in the therapeutic method as described above, the cells being exposed to an antigen optionally before or after removal of the cells.

The chronological sequence of presenting the immunization antigens, their uptake by antigen-presenting cells and furthermore the migration of these cells to local lymph nodes, where the substances that have been taken up are presented to activated T-cells, is also important in a therapeutic implementation. Therefore, the patient is preferably inoculated with the antigen, preferably even before isolation of the cells, in particular preferably at least 1, 2, 3, 4 or 5 days and/or at most 20, 16, 12, 10, 9, 8, 7, 6, 5, 4, 3, 2 or 1 week(s) before isolation of the cells. Alternatively, a subsequent vaccination or a treatment of the cells with an antigen in vitro or ex vivo is also possible.

In addition, it is also possible to use antigen-presenting cells, which preferably originate from the patient himself and can be contacted with the corresponding antigen and then contribute toward the increase in the specific immunoreactivity either jointly or shortly before or after the administration of Cbl-b-inhibited immune cells, preferably T-cells.

The cells are preferably specific for a certain antigen or cells comprising a certain antigen are selected for the specificity or presence of the antigen, where the immunoreactivity of the selected cells is increased. Through the selection of a certain antigen and/or cells with an immune-enhancing specificity herefor, an immune response can be directed against a certain target in a patient in a targeted manner. Such a target would be in particular a tumor (through the selection of at least one or more tumor antigens) or a pathogen.

It is conceivable that the corresponding siRNA in the transfection batch is already placed in the same sterile disposable tubes in parallel with the separation of the cells. Therefore, in another aspect, the present invention relates to a preferably sterile container, such as a disposable tube, comprising a Cbl-b inhibitor, in particular to increase the immunoreactivity of cells of the immune system to an antigen.

Likewise, the present invention proposes a kit, comprising a container, in particular a disposable tube for holding the cells of the immune system, as well as a Cbl-b inhibitor, such as siRNA, in particular to increase the immunoreactivity of cells of the immune system to an antigen by the method according to the invention.

The container and/or the kit may also comprise an immunostimulating substance, preferably cytokine(s) or ligands of other receptors (e.g., TLRs) or antibodies to surface molecules, preferably CD3 and/or CD28, to additionally enhance the stimulation. Likewise, the kit or the container may also comprise stabilizing components, media or buffers (for stabilization of the cells), transfection or nucleofection solutions, preferably cell media, such as RPMI or Optimem.

The present invention is illustrated by the following figures and examples without being limited thereto.

In the figures:

FIG. 1 shows a simplified schematic diagram of T-cell activation by co-stimulation (a), or in the case of attenuation of Cbl-b expression, by sole stimulation of the T-cell receptor (c), which does not usually lead to activation (b);

FIG. 2 shows a Western Blot analysis of Cbl-b expression. CD8+ cells were isolated from human PBMC, transfected with Cbl-b-siRNA, kept in culture and compared with a control group without, stimulation, after anti-CD3 stimulation or after anti-CD3 and anti-CD28 stimulation. Fyn was used as the loading control;

FIG. 3 shows the IFN-γ secretion of human CD8+ cells two days after siRNA treatment. The IFN-γ concentration was measured in supernatants of CD8+ T-cells without stimulation (medium) (left) and after CD3-specific co-stimulation (center) or after CD3 and CD28-specific co-stimulation (right. Two-day-old cell populations transfected by means of nonspecific siRNA ($1^{st}$ bar), Cbl-b-specific siRNA ($2^{nd}$ bar), c-Cbl-specific siRNA ($3^{rd}$ bar) and Cbl-b-specific and c-Cbl-specific siRNA ($4^{th}$ bar) were compared;

FIG. 4 shows the IL-2 secretion of human CD8+ cells twenty days after siRNA treatment. The IL-2 concentration in supernatants of CD8+ T-cells without stimulation (medium) (left) and after CD3-specific stimulation (center) or after CD3- and CD28-specific co-stimulation (right) was measured. Two-day-old cell populations transfected by means of nonspecific siRNA ($1^{st}$ bar), Cbl-b-specific siRNA ($2^{nd}$ bar), c-Cbl-specific siRNA (3rd bar) and Cbl-b-specific and c-Cbl-specific siRNA ($4^{th}$ bar) were compared; and FIG. 5 shows the chronological sequence of the in vitro Cbl-b attenuation batch to increase the immunoreactivity;

FIG. 7 shows the Cbl-b mRNA expression after RNAi (A) and the amount of Cbl-b protein produced after RNAi in a Western Blot (B);

EXAMPLES

Example 1

Sequences

The following siRNA sequences were used for inhibition of Cbl-b, alone or in combination:

1. Sense sequence:

(SEQ ID No. 1)
G.A.A.C.A.U.C.A.C.A.G.G.A.C.U.A.U.G.A.U.U

Antisense sequence:

(SEQ ID No. 2)
5'-P.U.C.A.U.A.G.U.C.C.U.G.U.G.A.U.G.U.U.C.U.U

2. Sense sequence:

(SEQ ID No. 3)
G.U.A.C.U.G.G.U.C.C.G.U.U.A.G.C.A.A.A.U.U

Antisense sequence:

(SEQ ID No. 4)
5'-P.U.U.G.C.U.A.A.C.G.G.A.C.C.A.G.U.A.C.U.U

3. Sense sequence:

(SEQ ID No. 5)
G.G.U.C.G.A.A.U.U.U.U.G.G.G.U.A.U.U.A.U.U

Antisense sequence:

(SEQ ID No. 6)
5'-P.U.A.A.U.A.C.C.C.A.A.A.A.U.U.C.G.A.C.C.U.U.

4. Sense sequence:

(SEQ ID No. 7)
U.A.U.C.A.G.C.A.U.U.U.A.C.G.A.C.U.U.A.U.U

Antisense sequence:

(SEQ ID No. 8)
5'-P.U.A.A.G.U.C.G.U.A.A.A.U.G.C.U.G.A.U.A.U.U

The following siRNA sequences were used alone or in combination to inhibit c-Cbl:

1. Sense sequence (SEQ ID No. 9)
A.A.U.C.A.A.C.U.C.U.G.A.A.C.G.G.A.A.A.U.U

Antisense sequence (SEQ ID No. 10)
5'-P.U.U.U.C.C.G.U.U.C.A.G.A.G.U.U.G.A.U.U.U.U 2. Sense sequence (SEQ ID No. 11)
G.A.C.A.A.U.C.C.C.U.C.A.C.A.A.U.A.A.A.U.U Antisense sequence (SEQ ID No. 12)
5'-P.U.U.U.A.U.U.G.U.G.A.G.G.G.A.U.U.G.U.C.U.U 3. Sense sequence (SEQ ID No. 13)
U.A.G.C.C.A.C.C.U.U.A.U.A.U.C.U.U.A.U.U Antisense sequence (SEQ ID No. 14)
5'-P.U.A.A.G.A.U.A.U.A.A.G.G.U.G.G.C.U.A.U.U 4. Sense sequence (SEQ ID No. 15)
G.G.A.G.A.C.A.C.A.U.U.U.C.G.G.A.U.U.A.U.U Antisense sequence (SEQ ID No. 16)
5'-P.U.A.A.U.C.C.G.A.A.A.U.G.U.G.U.C.U.C.C.U.U

Example 2

Transient Reduction in Cbl-b Expression

In this example, it will be shown that the immunoreactivity of T-cells can be influenced ex vivo.

Figure 1:
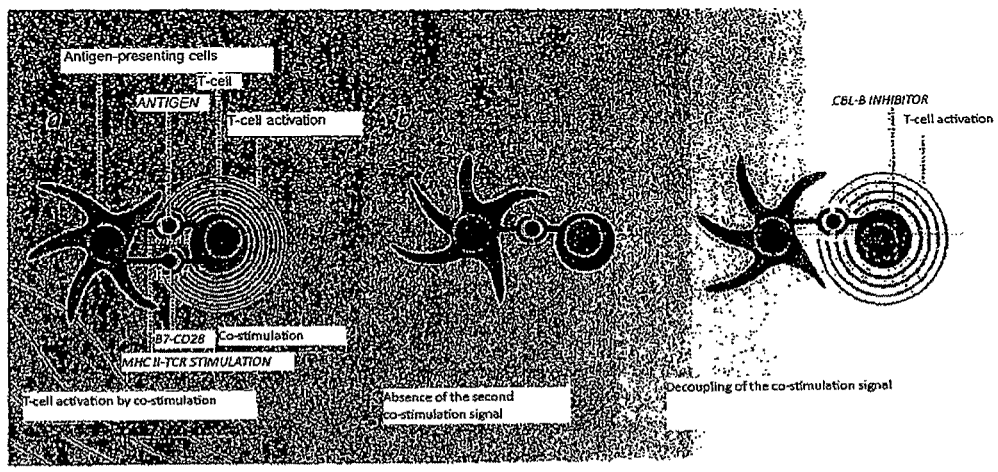
Figure 2:
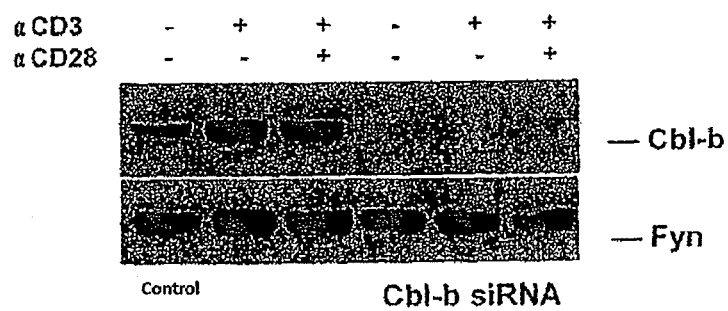

Whole blood was taken from a donor by using CPT tubes (Vacutainer), and the PBMCs were separated by centrifugation. In another step, CD8+ cells from this preparation were concentrated. These were transfected by means of a Cbl-b-specific siRNA using an Amaxa transfection apparatus (detailed protocol in Example 3) and cultured further. An identical batch with a nonspecific siRNA was transfected using the identical protocol by means of a Cbl-b-specific siRNA and cultured further as the control. Since a potential overlap of the function of Cbl-b and c-Cbl is assumed, two other batches were treated by c-Cbl-specific siRNA and a combination of c-Cbl-specific and Cbl-b-specific siRNA. All batches were cultured for two days. The fact that the transfection led to the desired attenuation of Cbl-b expression was demonstrated by subsequent Western Blot analysis. To induce Cbl-b expression, the cultures were stimulated with CD3 and in another batch with CD3-specific and CD28-specific antibodies. In all experiments, Cbl-b expression in the transfected preparation was forced to less than 5% of the intensity of a control transfection, as shown in FIG. 2. Since the stability of the siRNA and consequently an efficient suppression of expression is of a limited duration and is not transmitted to other cells, the selected batch is a transient attenuation of Cbl-b expression, which is bound strictly to the presence of the Cbl-b siRNA.

Example 3

Transfection Protocol

Nucleofection with siRNAs in Human T-Cells

Nucleofection is performed by working together with another lab assistant. One person performs the pipetting of the siRNA oligos and the other person transfers the specimens to a culture medium. This significantly accelerates the procedure.

1. Prepare the medium for the cell RPMI (+pen/strep., +L-glut, +10% FCS).
2. Pipet the culture medium into at least two 50 mL Falcon tubes/constructs (one for collecting the nucleofected cells and one for the cell washing medium), 1 mL/L nucleofection specimen into each tube. Bring the tubes to 37° C.
3. Mark the Eppendorf tubes for each nucleofection specimen.
4. Centrifuge the nucleofect cells (410 g) for seven minutes and remove the supernatant. Add Optimem (Gibco, #31985-047)
5. So that the cell density will be $40 \times 10^6$/mL. Pipet 100 μL ($=4 \times 10^6$ cells) into each Eppendorf tube.
6. Add 1.5-2.5 μM siRNA-oligo into the Eppendorf tubes containing the cells just prior to nucleofection. Mix by pipetting and transfer the solution to the cell (prevent air bubbles). Tap the cell against the table to remove the bubbles.
7. Close the cover and place the cell in the Amaxa transfection device (electroporator). (Program U-14 and not V-24 as the best option using Optimem Nucleofector solution). Push the x-button and remove the cell after the OK signal. (Push the x-button again before the next electroporation.)
8. Immediately add 500 μL RPMI (37° C.) to the nucleofection cell and mix cautiously by pipetting using the Pasteur pipette. Transfer the cells to the collecting Falcon tube. Wash the cell once with 500 μL preheated RPMI and transfer the remainder of the cells to the collecting Falcon tube.
9. Repeat steps 5-7 with each sample.
10. Place the Falcon tubes in the incubator until all specimens have been nucleofected.
11. Pipet 4 mL of the cell suspension into 6-well plate wells (=2 specimens) and place the plates in the incubator.
12. The next day, collect the cells, count them and start the culture 24 hours after the nucleofection performed as described above. Take an aliquot of the cells for isolation of RNA to check on whether the target gene has been downregulated as of the time of activation. The protein specimens are taken on the basis of the protein expression kinetics.

Example 4

Nucleofection Efficiency

CD8+ was isolated from human peripheral blood as described above. The negative selection was performed using beads.
Result (Amaxa Comparison):
Purity of the population: 97% CD8+ (FACS)

| Device | Viability after 3.5 h Trypan-blue negative (%) | Viability after 24 h Trypan-blue negative (%) | Efficiency siGlo pos in FACS (%) |
|---|---|---|---|
| Amaxa V-24 | 94 | 93 | 96 |
| Untreated | 100 | 99 | 0 |

Experiment with Optimem:

| Nucleofection in | Program | Cells thereafter in | Viability after 3.5 h Trypan-blue negative (%) | Viability after 24 h Trypan-blue negative (%) | Efficiency siGlo pos in FACS (%) |
|---|---|---|---|---|---|
| Nucleofector solution | V-24 | hTC | 99 | 92 | 96 |
| Optimem | V-24 | RMPI | 92 | 67 | 96 |
| Optimem | U-14 | RMPI | 95 | 92 | 96 |

Thus a definitely reduced expression of Cbl-b was detected in the protein chemistry.

Example 5

Transient Increase in T-Cell Reactivity—Measurement of IFN-γ

Figure 3:
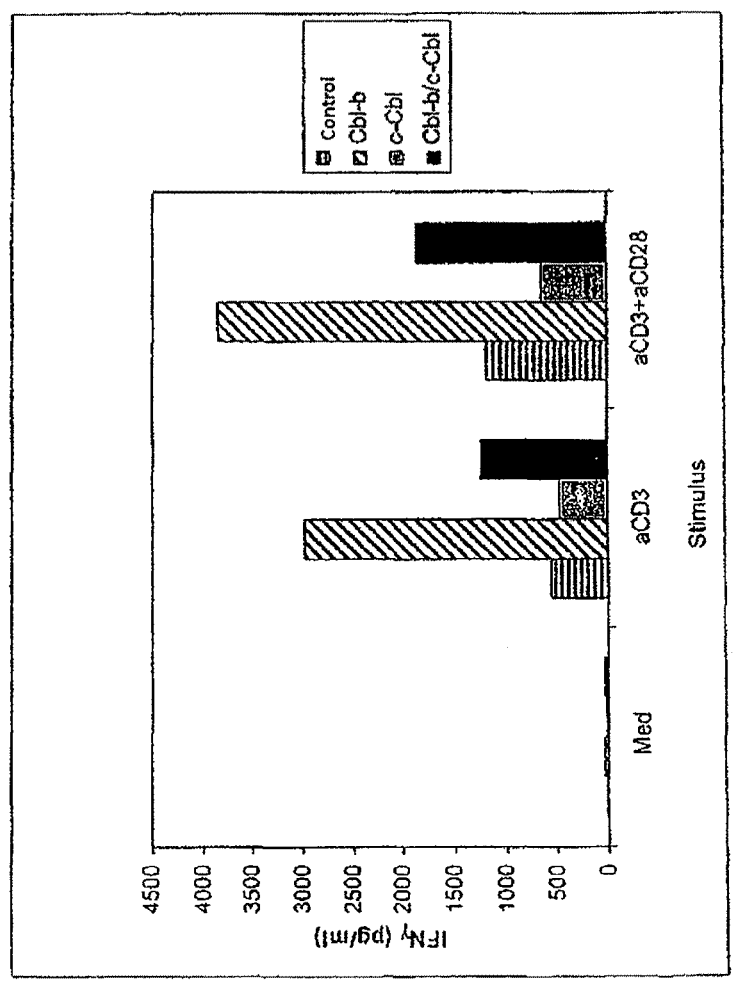

It was thus demonstrated that Cbl-b expression in human CD8+ cells can be suppressed with at least 95% efficiency. As another consequence, it will now be demonstrated that the reactivity of the T-cell population can also be increased. To be sure that the desired effect is exclusively Cbl-b-specific and cannot be bypassed in the event of attenuation of Cbl-b expression by c-Cbl, in another approach, c-Cbl was also attenuated, and in a third batch c-Cbl and Cbl-b were attenuated. All these CD8+ cell cultures were cultured for two days and were stimulated by CD3 and also by CD3 and CD28 and compared with an unstimulated group. Normally T-cells require this co-stimulation of CD3 and CD28 to proliferate, which can be detected easily by secretion of inflammatory cytokines in the supernatants of the cultures. To detect this T-cell activation, IFN-γ titers in the supernatants were measured. A graphic plot of the influence of the attenuation of expression by siRNA treatment on the T-cell reactivity is shown in FIG. 3. Two days after transfection, all CD8+ cell cultures were transfected with Cbl-b and/or c-Cbl-specific siRNA, stimulated as described and compared with a control group that had been transfected with a nonspecific siRNA. Unstimulated cells had essentially no IFN-γ expression. After exclusive CD3 stimulation, all cultures had an elevated reactivity, so that at least 500 pg/mL IFN-γ could be detected in the supernatants. The signals for c-Cbl-specific siRNA and nonspecifically transfected cells were very similar (low). Only cells transfected with Cbl-b-specific siRNA had a much higher reactivity, which was associated with an IFN-γ titer of approximately 3 ng/mL. The reactivity of the cell preparation co-transfected by c-Cbl- and Cbl-b-specific siRNA, however, was lower than that after Cbl-b-specific siRNA treatment, reaching only 1.2 ng/mL. In all cases, CD3- and CD28-specific co-stimulation yielded, as expected, definitely higher signals than just CD3-specific stimulation. The control preparation, which was treated with nonspecific siRNA, yielded an IFN-γ titer in an amount of 1.2 ng/mL, while the culture treated with Cbl-b-specific siRNA had an IFN-γ concentration of 3.8 ng/mL. It was noteworthy that the Cbl-b and c-Cbl-specific co-attenuated culture had titers of 1.7 ng/mL, which were thus much lower than those in the Cbl-b-attenuated group. It was also unexpected that the cell population, which was treated with c-Cbl-specific siRNA had a significantly lower reactivity and only 500 pg/mL IFN-γ was measured in the supernatant. This concentration is significantly lower than that of the nonspecifically treated co-stimulated control group and is comparable to the values of the control group stimulated only with anti-CD3. Thus, in contrast with the murine system, a redundancy of Cbl-b and c-Cbl in human CD8+ T-cells was ruled out experimentally and a therapeutic approach via Cbl-b (and its upstream regulators) but not via Cbl-b/c-Cbl combinations is appropriate to increase immunoreactivity. However, inhibition of c-Cbl allows immunesuppression for other applications, such as the treatment of inflammations or allergies.

This concomitant therapeutic approach, designed either as monotherapy or combined with vaccination, is also capable of recognizing disseminated tumor cells in the periphery and combating them in the long run by building up an immune response. When used immediately after a cancer has been diagnosed, dissemination of a primary tumor is also thereby prevented.

Example 6

Transient Increase in T-Cell Reactivity—Measurement of IL-2

Figure 4:
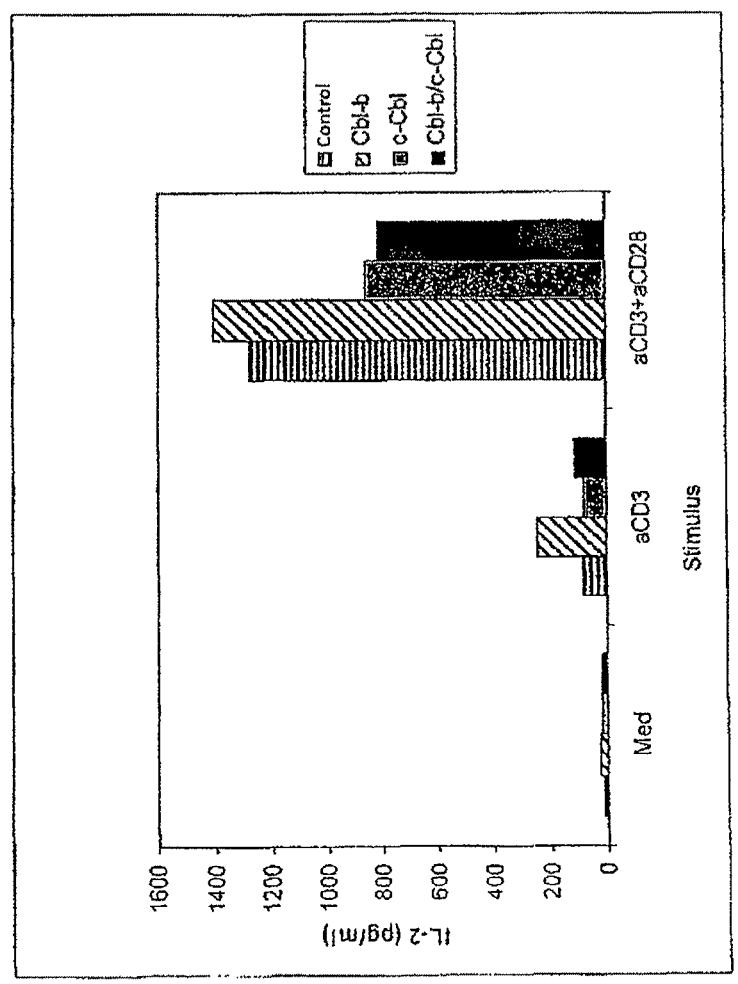

A very similar result was obtained by measuring the IL-2 concentrations in the same supernatants, as can be seen from FIG. 4. Without stimulation, there was no measurable response, whereas an anti-CD3-specific treatment led to a definitely measurable signal in all groups. Thus >200 pg/mL was measured in the Cbl-b-attenuated group. The IL-2 concentration in the Cbl-b and c-Cbl-co-attenuated population was again much lower and amounted to <100 pg/mL. The anti-CD3 and anti-CD28-specific co-stimulation in turn yielded higher signals. IL-2 concentrations of >800 pg/mL were measured in all groups, regardless of the SiRNA treatment. The control group yielded titers very similar to the Cbl-b-attenuated titers of 1.3 and 1.4 ng/mL. It is interesting that the IL-2 concentrations after c-Cbl-specific attenuation were much lower and amounted to only 800 pg/mL, regardless of whether only c-Cbl was used exclusively or c-Cbl was used together with Cbl-b in this approach.

Example 7

Transient Increase in Immunoreactivity

Due to the in vitro or ex vivo treatment, T-cell reactivity is efficiently increased, so it is possible through exclusive stimulation of the T-cell receptor to induce the proliferation of T-cells. This is an essential prerequisite for the therapeutic approach described here. This attenuation is of a transient nature due to the use of RNAi technology.

Figure 5:
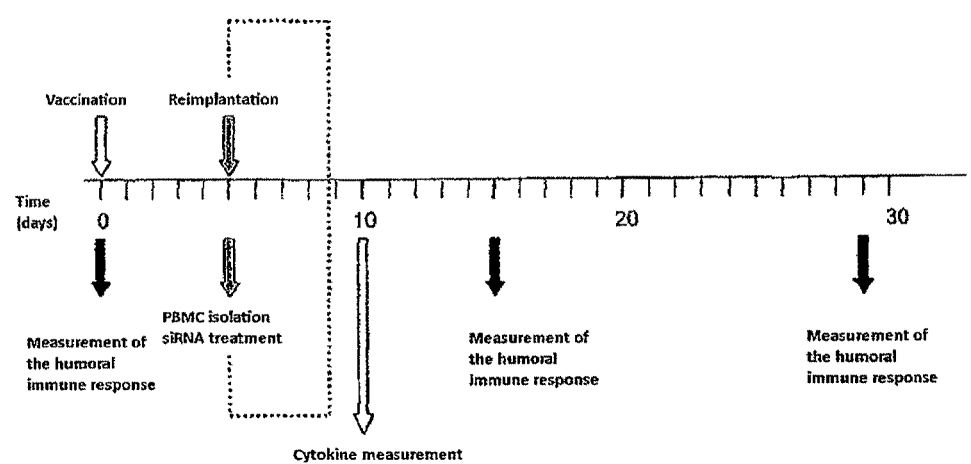

This applicability of these modified cells serves to increase the immunogenicity of vaccines and to increase the reactivity of the immune system in general. Five days after a basic immunization, whole blood is taken from a patient in CPT tubes. After approx. twenty minutes, PBMCs are isolated by centrifugation. The cell preparations are transfected with Cbl-b-specific siRNAs and re-implanted in the patient immediately thereafter. On day 10, whole blood was again taken and serum was extracted. Pro-inflammatory cytokine titers were measured in this serum and compared with the control group. The nature of the immune response induced is also analyzed with regard to the cellular orientation of a Th1-controlled immune response (elevated IFN-γ, IL-2 and IL12 titers) or a humoral trend in a Th2-directed immune response (elevated IL4, IL5 and IL10 titer). If necessary, other booster immunizations with or without PBMC therapy, are performed in a 14-day interval (FIG. 5).

Example 8

Nucleofection of CD4 T-Cells and CD19 B-Cells

Figures 6A, 6B:
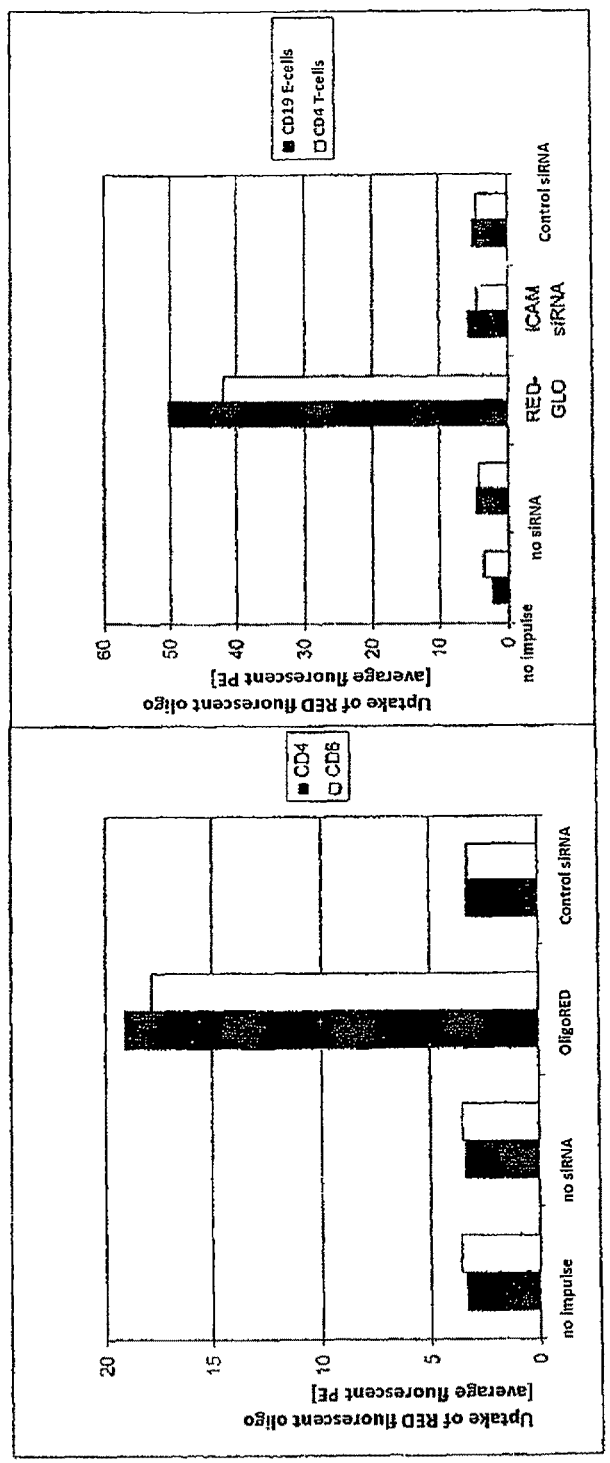
FIG. 6 shows the siRNA uptake by human T cells, isolated from PBMCs (A), and the siRNA uptake by CD8-cell-depleted PBMCs (B)

PBMCs were isolated as described above and were transfected under the same conditions as in Example 3 (U14). The oligo used for transfection (siGLO red) was used in a concentration of 2 µM, and the specific uptake was detected by FACS; the differentiation of CD4 and CD8 cells was performed by simultaneous double staining with CD8-TIFC and CD3-APC (FIG. 6A).

PBMCs were prepared as described above and their CD8 cells were isolated. The remaining CD8-negative cells were then transfected again with siGLO red as described above (although with an oligo concentration of 3.3 µM). The specific uptake was detected by FACS by simultaneous double staining with CD3-FITC and CD19-APC (FIG. 6B). It is interesting that it was also observed in this experiment that efficient uptake of the oligos used also occurred in the fraction of CD3/CD19-negative lymphocytes, which consist mainly of NK cells.

This example therefore shows that other immune cells can also be transfected highly efficiently under the same transfection conditions as the CD8 cells.

Example 9

Transient Reduction in the Cbl-b Expression in Human CD4 Cells on an mRNA and Protein Level CD4 cells were isolated from PBMCs by depletion of CD8 cells and cultured by PHA/anti-CD3/28 stimulation. After two weeks, these CD4 cells were transfected by a Cbl-b-specific siRNA using the Amaxa transfection protocol (see Examples 3 and 8). An identical batch was transfected with a nonspecific siRNA using the identical protocol as the control batch. After transfection, the cells were cultured with IL-2 (5 ng/mL) for one more day and stimulated with anti-CD3/28 the next day.

The Cbl-b mRNA expression in the transfected preparation was reduced by approximately 85% in comparison with the control transfection in the CD4 cells stimulated for 24 h (FIG. 7A). The sharp reduction in Cbl-b mRNA correlated with a comparatively strong reduction in the amount of protein of Cbl-b, as detected in the Western Blot (FIG. 7B).

Example 10

Increase in CD4 T-Cell Reactivity—Measurement of Cytokines with Anti-Tumor Activity One of the main tasks of CD4-cells in a T-cell-mediated immune response is production of inflammatory cytokines. The literature mentions in particular the cytokines IL-2, IFN-γ and TNF-α in particular.

Figure 8:
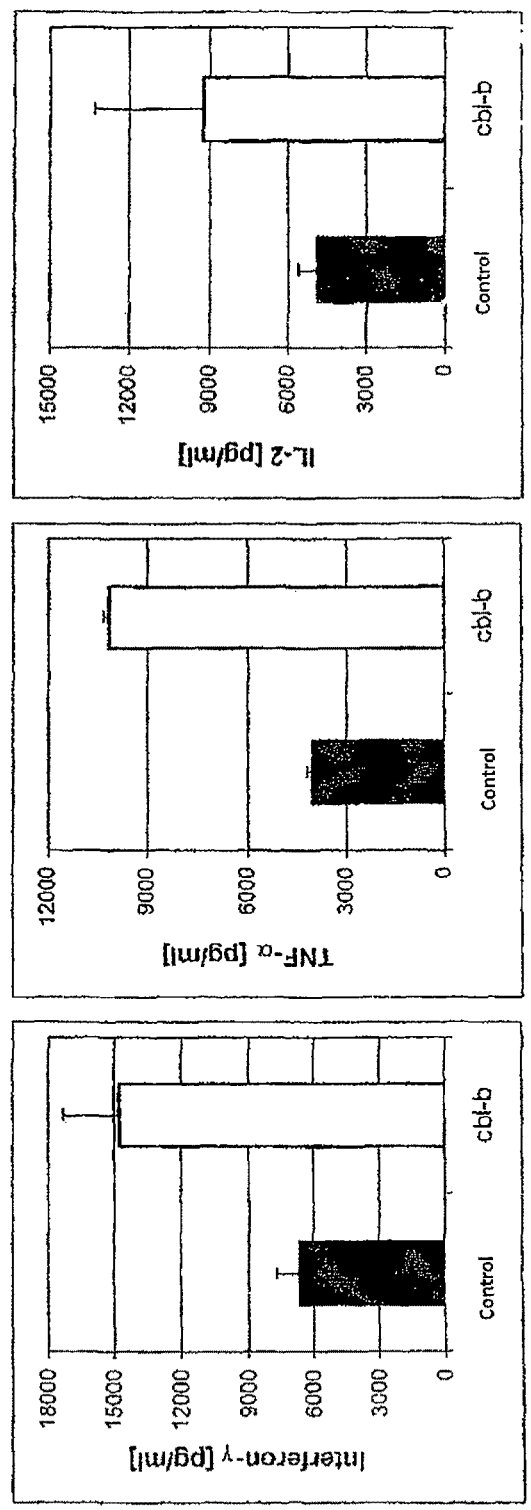
FIG. 8 shows the IFN-γ, TNF-α, IL-2 production after Cbl-b inhibition.

The expression of these three cytokines was therefore determined by ELISA. At the time 24 h after anti-CD2/28 stimulation, these three cytokines were significantly elevated in human Cbl-b-silenced CD4 T-cells (FIG. 8).

Example 11

Transient Course of the Increase in CD4 T-Cell Reactivity Through Increased Production of Cytokines with Anti-Tumor Activity To achieve efficient anti-tumor activity of Cbl-b-silenced T-cells, it is important for the increased cytokine production to also remain upheld over a certain period of time after T-cell stimulation. However, this period of time should also be limited in order to minimize the risk of permanently establishing an unwanted autoimmunity to the patient's nonmalignant tissue.

Figure 9:
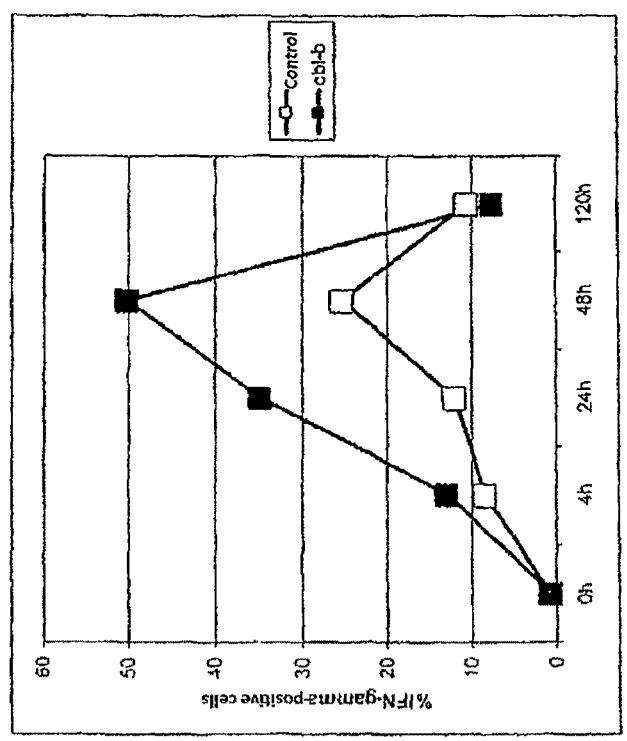
FIG. 9 shows the IFN-γ production after Cbl-b inhibition as a time profile.

Therefore, production of IFN-γ was also analyzed by intracellular staining in FACS at various points in time. The diagram in FIG. 9 shows clearly that the marked increase in IFN-γ was maintained for at least 48 h, but six days after stimulation it dropped back to a level comparable to that in the controls.

Example 12

Increase in T-Cell Reactivity—Increased Expression of Surface Molecules with Functional Properties and/or Stimulation Marker Function The respective determination of cytokine production as a marker for functionally successful silencing of Cbl-b in human T-cells is technically more complex and therefore it tends to not be executable so closely in time. The expression of functionally important surface markers by FACS was therefore also determined.

Figure 10A:
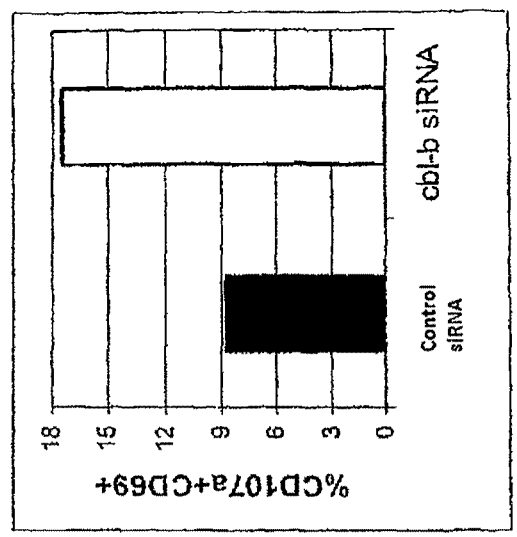
FIG. 10 shows the increase in T-cell reactivity measured by CD107a+CD69 (A), CD107a, CD3, CD40L, ICAM (B) marker expression.

CD107a is defined in the literature as a surface marker for secretory activity of cytotoxic T-cells and was therefore determined on Cbl-b-suppressed CD8 T-cells after 24 h of anti-CD3/28 stimulation. The T-cells transfected with Cbl-b siRNA therefore manifested a greatly elevated secretory activity (FIG. 10A).

Figure 10B:
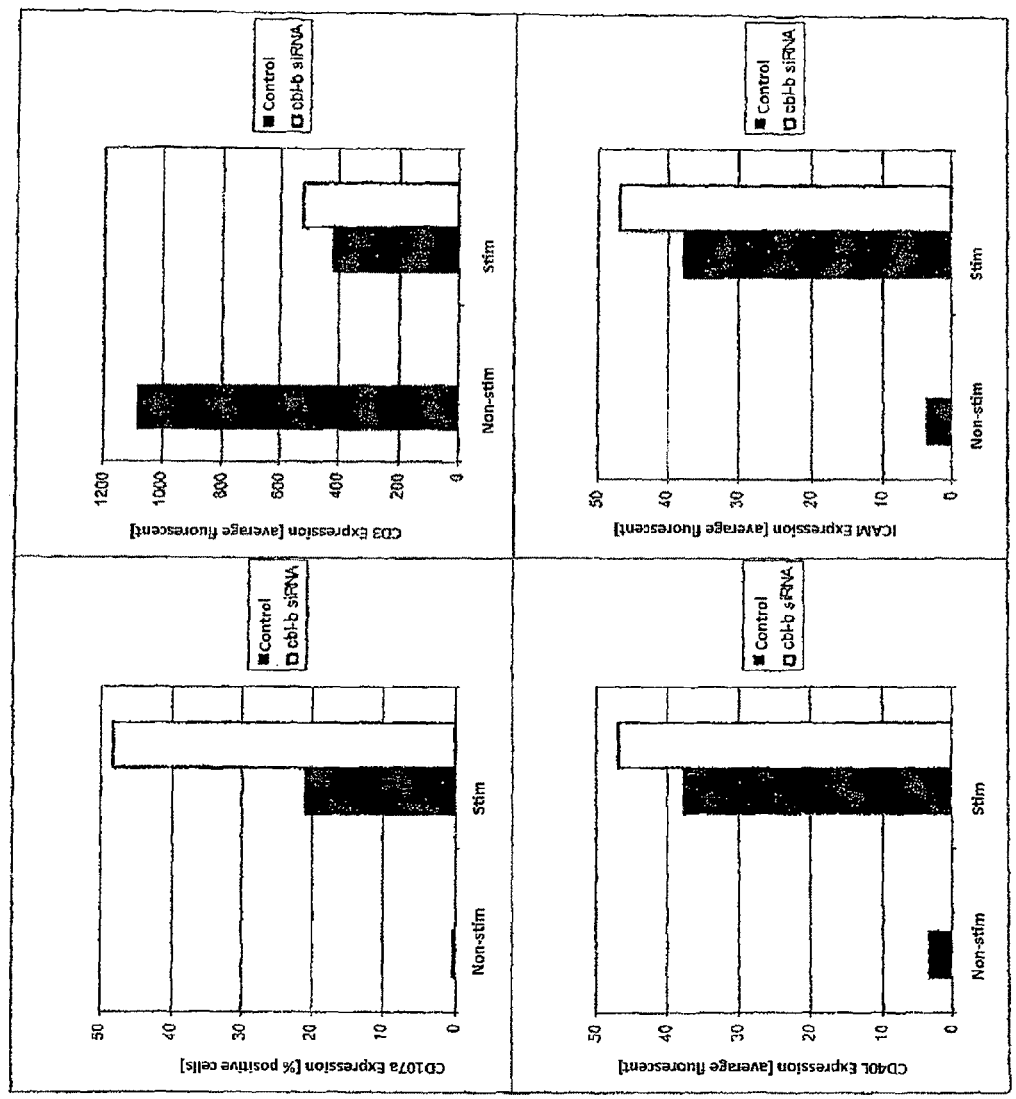

Since the CD107a molecule is involved in the vesicular transport in T-cells, it may also be used as the principal marker for the secretory activity of CD4 T-cells. FIG. 10B shows that expression of CD107a in Cbl-b-siRNA-transfected cells was also significant in comparison with that of control cells treated otherwise the same.

CD40L and ICAM are two other surface molecules that can be induced by T-cell stimulation. These two molecules are of functional relevance, CD40L in particular for interaction with antigen-presenting cells and for stimulation/proliferation of B-cells, ICAM for the interaction with antigen-presenting cells and migration out of the vascular system into (malignant) tissue. FIG. 10B shows that expression of these two surface molecules was significantly elevated in Cbl-b-siRNA-transfected human CD4 T-cells.

One of the mechanisms described here as responsible for the increase in T-cell reactivity is the less pronounced attenuation of CD3-receptors on the cell surface. FIG. 10B shows that the amount of CD3 receptors still on the cell surface was also definitely elevated in Cbl-b-siRNA-transfected human CD4 T-cells.

It is interesting that the cell surface expression of the traditional T-cell activation marker CD69 was also definitely elevated, whereas the expression of CD25 remained unchanged. This may be of particular functional relevance, because although CD25 is also defined as a stimulation marker, its function is especially associated with the presence and survival of so-called T-regulatory cells.

On the whole, FIG. 10 therefore shows that additional functionally important molecules or molecules which serve as surface markers can be detected in clearly larger amounts on the cell surface by Cbl-b-siRNA transfection.

Example 13

Figure 11A:
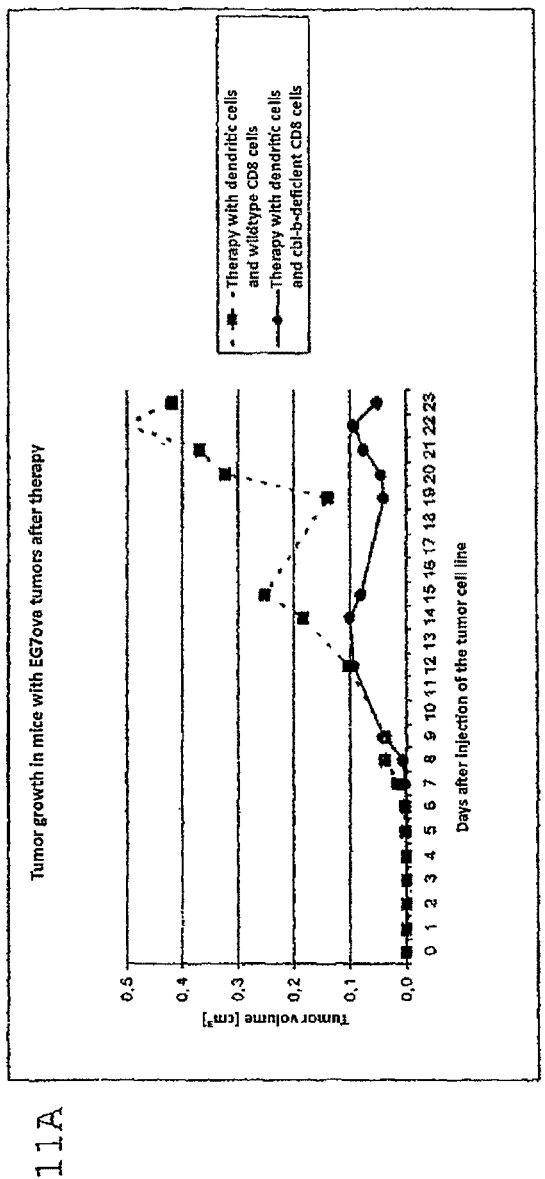
FIG. 11A shows tumor growth in mice after treatment, with/without Cbl-b suppression in therapeutic CD8 cells; B: Mortality of mice with EG7ova tumors after treatment.

The Joint Transfer of Cbl-b-Deficient T-Cells and Dendritic Cells is an Effective Therapeutic Procedure in an In Vivo Tumor Model A tumor was induced in wild-type mice by subcutaneous injection of 0.1 million EG7ova cells. Then CD8 T-cells and dendritic cells were injected on days 5 and 6 and the effect of this adoptive cell therapy was tracked continuously by measuring the growth of the tumor. FIG. 11A shows that tumor growth could be suppressed much more strongly and for a longer period of time by the transfer of Cbl-b-deficient T-cells than by wild-type T-cells.

Figure 11B:
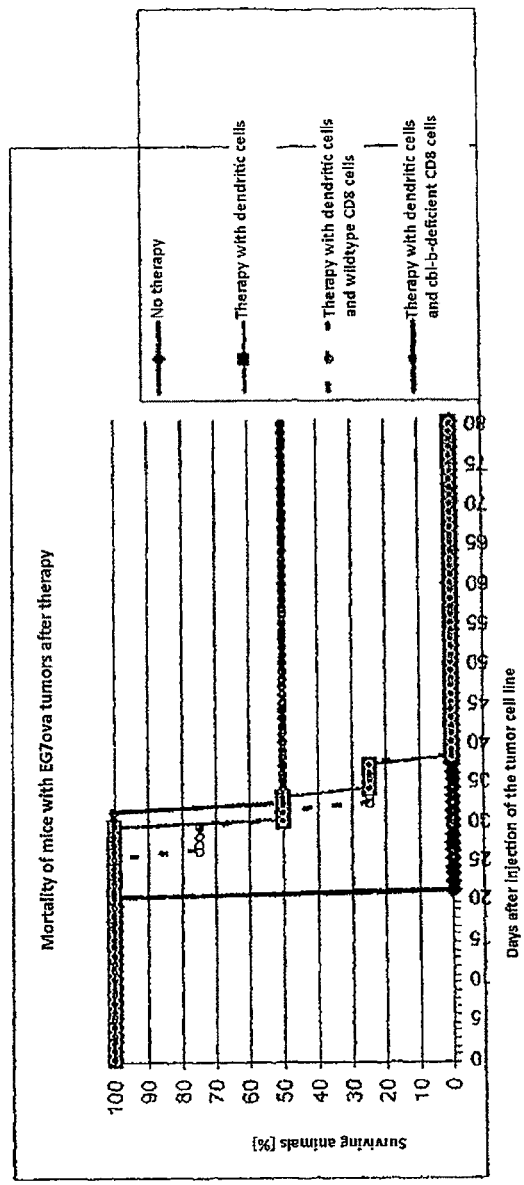

FIG. 11B also shows that the treatment with Cbl-b-deficient T-cells ensured a long-term survival of a significant portion of the treated mice until the end of the observation period of 80 days. In contrast with that, treatment with wild-type T-cells led to only a slightly longer life expectancy in comparison with the control group. Therefore, FIG. 11B shows that treatment with Cbl-b-deficient or inhibited T-cells has a significant advantage in comparison with treatment with normal T-cells.

The invention claimed is:

1. A method of increasing immunoreactivity in a patient comprising:
   isolating at least one immune system cell from the patient;
   treating the cell, in vitro or ex vivo, with at least one Cbl-b inhibitor or antagonist to increase immunoreactivity of the cell; and
   reimplanting the cell in the patient;
   wherein the immune system cell is selected from the group consisting of antigen presenting cells, PBMCs, T-lymphocytes, B-lymphocytes, monocytes, macrophages, NK cells, NKT cells and dendritic cells;
   wherein the Cbl-b inhibitor or antagonist is selected from the group consisting of a short DNA sequence complementary to a part of the Cbl-b mRNA sequence and a short RNA sequence complementary to a part of the Cbl-b mRNA sequence; wherein the cell has optionally been contacted with an antigen; and
   wherein the immunoreactivity in the patient is increased by a transient reduction in or inhibition of the Cbl-b function of the cell.

2. The method of claim 1, wherein the patient has a congenital or acquired immunoinsufficiency, multiple myeloma, chronic lymphatic leukemia, drug-induced immunosuppression, or a cancer.

3. The method of claim 2, wherein the patient has AIDS.

4. The method of claim 2, wherein the patient has a cancer.

5. The method of claim 4, wherein the cancer is a solid tumor.

6. The method of claim 4, further comprising administering to the patient another anti-cancer treatment.

7. The method of claim 6, wherein the other anti-cancer treatment comprises chemotherapy, radiotherapy, administration of a biologic, or dendritic cell-supported vaccination.

8. The method of claim 7, wherein the other anti-cancer treatment comprises tumor vaccination.

9. The method of claim 1, further comprising vaccinating the patient with the antigen.

10. The method of claim 9, wherein the patient is vaccinated before the isolation of the cell.

11. The method of claim 10, wherein the patient is vaccinated at least two days and/or at most eight weeks before isolation of the cell.

12. The method of claim 1, wherein the cell has been contacted with an antigen in vitro or ex vivo.

13. The method of claim 1, wherein treating the cell, in vitro or ex vivo, with at least one Cbl-b inhibitor or antagonist to increase immunoreactivity of the cell is accomplished by a method of increasing immunoreactivity of an immune system cell that has been contacted with an antigen comprising reducing and/or inhibiting Cbl-b function in the cell, wherein immunoreactivity of the cell to the antigen is increased.

14. The method of claim 1, wherein the cell is a cell specific for the antigen or a cell comprising the antigen.

15. The method of claim 14, wherein the antigen is a tumor antigen.

16. The method of claim 1, further comprising expanding the cell before reimplantation.

17. The method of claim 1, wherein the immune system cell is selected from the group consisting of PBMCs and T-lymphocytes.

18. The method of claim 1, wherein the immune system cell is selected from the group consisting of T-lymphocytes, B-lymphocytes, and NK cells.

19. The method of claim 1, wherein the immune system cell is selected from the group consisting of T-lymphocytes and monocytes.

20. The method of claim 1, wherein the immune system cell is selected from the group consisting of T-lymphocytes, NK cells, and monocytes.

* * * * *

SEQUENCE LISTING

```
<160> NUMBER OF SEQ ID NOS: 16

<210> SEQ ID NO 1
<211> LENGTH: 21
<212> TYPE: RNA
<213> ORGANISM: Artificial
<220> FEATURE:
<223> OTHER INFORMATION: RNAi

<400> SEQUENCE: 1
gaacaucaca ggacuaugau u                                              21

<210> SEQ ID NO 2
<211> LENGTH: 21
<212> TYPE: RNA
<213> ORGANISM: Artificial
<220> FEATURE:
<223> OTHER INFORMATION: RNAi

<400> SEQUENCE: 2
ucauaguccu gugauguucu u                                              21
```

```
<210> SEQ ID NO 3
<211> LENGTH: 21
<212> TYPE: RNA
<213> ORGANISM: Artificial
<220> FEATURE:
<223> OTHER INFORMATION: RNAi

<400> SEQUENCE: 3
guacuggucc guuagcaaau u                                              21

<210> SEQ ID NO 4
<211> LENGTH: 21
<212> TYPE: RNA
<213> ORGANISM: Artificial
<220> FEATURE:
<223> OTHER INFORMATION: RNAi

<400> SEQUENCE: 4
uuugcuaacg gaccaguacu u                                              21

<210> SEQ ID NO 5
<211> LENGTH: 21
<212> TYPE: RNA
<213> ORGANISM: Artificial
<220> FEATURE:
<223> OTHER INFORMATION: RNAi

<400> SEQUENCE: 5
ggucgaauuu uggguauuau u                                              21

<210> SEQ ID NO 6
<211> LENGTH: 21
<212> TYPE: RNA
<213> ORGANISM: Artificial
<220> FEATURE:
<223> OTHER INFORMATION: RNAi

<400> SEQUENCE: 6
uaauacccaa aauucgaccu u                                              21

<210> SEQ ID NO 7
<211> LENGTH: 21
<212> TYPE: RNA
<213> ORGANISM: Artificial
<220> FEATURE:
<223> OTHER INFORMATION: RNAi

<400> SEQUENCE: 7
uaucagcauu uacgacuuau u                                              21

<210> SEQ ID NO 8
<211> LENGTH: 21
<212> TYPE: RNA
<213> ORGANISM: Artificial
<220> FEATURE:
<223> OTHER INFORMATION: RNAi

<400> SEQUENCE: 8
uaagucguaa augcugauau u                                              21

<210> SEQ ID NO 9
<211> LENGTH: 21
<212> TYPE: RNA
<213> ORGANISM: Artificial
<220> FEATURE:
<223> OTHER INFORMATION: RNAi
```

-continued

<400> SEQUENCE: 9
aaucaacucu gaacggaaau u                                              21

<210> SEQ ID NO 10
<211> LENGTH: 21
<212> TYPE: RNA
<213> ORGANISM: Artificial
<220> FEATURE:
<223> OTHER INFORMATION: RNAi

<400> SEQUENCE: 10
uuuccguuca gaguugauuu u                                              21

<210> SEQ ID NO 11
<211> LENGTH: 21
<212> TYPE: RNA
<213> ORGANISM: Artificial
<220> FEATURE:
<223> OTHER INFORMATION: RNAi

<400> SEQUENCE: 11
gacaaucccu cacaauaaau u                                              21

<210> SEQ ID NO 12
<211> LENGTH: 21
<212> TYPE: RNA
<213> ORGANISM: Artificial
<220> FEATURE:
<223> OTHER INFORMATION: RNAi

<400> SEQUENCE: 12
uuuauuguga gggauugucu u                                              21

<210> SEQ ID NO 13
<211> LENGTH: 21
<212> TYPE: RNA
<213> ORGANISM: Artificial
<220> FEATURE:
<223> OTHER INFORMATION: RNAi

<400> SEQUENCE: 13
uagcccaccu uauaucuuau u                                              21

<210> SEQ ID NO 14
<211> LENGTH: 21
<212> TYPE: RNA
<213> ORGANISM: Artificial
<220> FEATURE:
<223> OTHER INFORMATION: RNAi

<400> SEQUENCE: 14
uaagauauaa gguggggcuau u                                             21

<210> SEQ ID NO 15
<211> LENGTH: 21
<212> TYPE: RNA
<213> ORGANISM: Artificial
<220> FEATURE:
<223> OTHER INFORMATION: RNAi

<400> SEQUENCE: 15
ggagacacau uucggauuau u                                              21

<210> SEQ ID NO 16

```
<211> LENGTH: 21
<212> TYPE: RNA
<213> ORGANISM: Artificial
<220> FEATURE:
<223> OTHER INFORMATION: RNAi

<400> SEQUENCE: 16
uaauccgaaa ugugucuccu u                                                    21
```